US00PP31422P2

(12) United States Plant Patent
van Veen

(10) Patent No.: US PP31,422 P2
(45) Date of Patent: Jan. 28, 2020

(54) ***ASTILBE* PLANT NAMED 'VISION VULCANO'**

(50) Latin Name: ***(Astilbe chinensis* x *Astilbe japonica)* X *Astilbe* x *arendsii***
Varietal Denomination: Vision Vulcano

(71) Applicant: Wilhelmus Franciscus van Veen, Erica (NL)

(72) Inventor: Wilhelmus Franciscus van Veen, Erica (NL)

(73) Assignee: FUTURE PLANTS LICENTIE B.V., Lisserbroek (NL)

( * ) Notice: Subject to any disclaimer, the term of this patent is extended or adjusted under 35 U.S.C. 154(b) by 0 days.

(21) Appl. No.: 16/501,265

(22) Filed: Mar. 14, 2019

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
CPC ..... A01H 5/02; A01H 6/80
See application file for complete search history.

*Primary Examiner* — Annette H Para
(74) *Attorney, Agent, or Firm* — C.A. Whealy

(57) ABSTRACT

A new and distinct cultivar of *Astilbe* plant named 'Vision Vulcano', characterized by its broadly upright and strong plant habit; strong and healthy foliage; freely, uniformly and remontant flowering habit with inflorescences positioned above the foliar plane; flowers that are red purple in color that fade to purple with development; and good garden performance.

2 Drawing Sheets

Botanical designation: (*Astilbe chinensis* x *Astilbe japonica*) X *Astilbe* x *arendsii.*

Cultivar denomination: 'VISION VULCANO'.

BACKGROUND OF THE INVENTION

The present invention relates to a new and distinct cultivar of *Astilbe* plant, botanically known as (*Astilbe chinensis* x *Astilbe japonica*) X *Astilbe* x *arendsii* and hereinafter referred to by the name 'Vision Vulcano'.

The new *Astilbe* plant is a product of a planned breeding program conducted by the Inventor in Noorden, The Netherlands. The objective of the breeding program was to create new uniform and strong *Astilbe* plants with attractive leaf and flower coloration.

The new *Astilbe* plant originated from a cross-pollination made by the Inventor in June, 2005 in Noorden, The Netherlands, of an unnamed proprietary selection of *Astilbe chinensis* x *Astilbe japonica*, not patented, as the female, or seed, parent with *Astilbe* x *arendsii* 'Weisse Gloria', not patented, as the male, or pollen, parent. The new *Astilbe* plant was discovered and selected by the Inventor as a single flowering plant within the progeny of the stated cross-pollination in a controlled environment in Noorden, The Netherlands in June, 2012.

Asexual reproduction of the new *Astilbe* plant by divisions in a controlled environment in Noorden, The Netherlands since June, 2012, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Vision Vulcano'. These characteristics in combination distinguish 'Vision Vulcano' as a new and distinct *Astilbe* plant:

1. Broadly upright and strong plant habit.
2. Strong and healthy foliage.
3. Freely, uniformly and remontant flowering habit with inflorescences positioned above the foliar plane.
4. Flowers that are red purple in color that fade to purple with development.
5. Good garden performance.

Plants of the new *Astilbe* differ primarily from plants of the female parent selection in the following characteristics:

1. Plants of the new *Astilbe* are shorter than plants of the female parent selection.
2. Inflorescences of plants of the new *Astilbe* are more upright and have narrower branch angles than plants of the female parent selection.

Plants of the new *Astilbe* differ primarily from plants of the male parent, 'Weisse Gloria', in flower color as flowers of plants of the new *Astilbe* are red purple in color becoming closer to purple with development whereas flowers of plants of 'Weisse Gloria' are white in color.

Plants of the new *Astilbe* can be compared to plants of *Astilbe chinensis* 'Vision in Red', disclosed in U.S. Plant Pat. No. 11,965. In side-by-side comparisons, plants of the new *Astilbe* differ from plants of 'Vision in Red' in the following characteristics:

1. Plants of the new *Astilbe* are shorter than plants of the 'Vision in Red'.
2. Inflorescences of plants of the new *Astilbe* are more upright and have narrower branch angles than plants of 'Vision in Red'.

3. Plants of the new *Astilbe* and 'Vision in Red' differ in flower color as flowers of plants of the new *Astilbe* fade to a darker purple color than flowers of plants of 'Vision in Red'.

Plants of the new *Astilbe* can also be compared to *Astilbe* x *arendsii* 'Gloria Purpurea', not patented. Plants of the new *Astilbe* and 'Gloria Purpurea' differ primarily in flower color as flowers of plants of the new *Astilbe* are red purple in color becoming closer to purple with development whereas flowers of plants of 'Gloria Purpurea' are pink in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Vision Vulcano' grown in a container.

The photograph on the second sheet is a close-up view of a typical inflorescence of 'Vision Vulcano'.

DETAILED BOTANICAL DESCRIPTION

The aforementioned photographs and following observations, measurements and values describe plants grown during the early summer in ground beds and 21-cm containers in an outdoor nursery in Lisserbroek, The Netherlands and under cultural practices typical of commercial *Astilbe* production. During the production of the plants, day temperatures ranged from 16° C. to 32° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: (*Astilbe chinensis* x *Astilbe japonica*) X *Astilbe* x *arendsii* 'Vision Vulcano'.

Parentage:

*Female, or seed, parent*.—Unnamed proprietary selection of *Astilbe chinensis* x *Astilbe japonica*, not patented.

*Male, or pollen, parent*.—*Astilbe* x *arendsii* 'Weisse Gloria', not patented.

Propagation:

*Type*.—By divisions.

*Time to initiate roots, summer*.—About 30 days at temperatures about 18° C.

*Time to produce a rooted young plant, summer*.—About eight months at temperatures about 20° C.

*Root description*.—Fine, moderately fibrous; typically whitish to greyed orange in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; broadly upright and strong plant habit; flowering stems and leaves basal; dense and bushy growth habit; moderately vigorous growth habit; moderate growth rate; freely, uniformly and remontant flowering habit with numerous flowers on branched panicles positioned above the foliar plane.

*Plant height* (*soil level to top of foliar plane*).—About 32.5 cm.

*Plant height* (*soil level to top of inflorescences*).—About 67.8 cm.

*Plant width* (*spread*).—About 52.4 cm.

*Stem description*.—Length: About 19.8 cm. Diameter: About 4 mm. Internode length: About 11.9 cm. Strength: Strong. Aspect: About 5° from vertical. Texture and luster: Sparsely pubescent; glossy. Color: Close to N199C; with development, close to 200B.

Leaf description:

*Arrangement*.—Alternate; biternately compound; up to 21 leaflets per leaf develop.

*Leaf length* (*excluding petiole*).—About 34 cm.

*Leaf width*.—About 29.7 cm.

*Terminal leaflet length*.—About 6.7 cm.

*Terminal leaflet width*.—About 4.5 cm.

*Lateral leaflet length*.—About 5.1 cm.

*Lateral leaflet width*.—About 3.3 cm.

*Leaf shape*.—Broadly ovate to broadly deltoid in overall outline.

*Lateral and terminal leaflet shape*.—Ovate to broadly elliptic.

*Lateral and terminal leaflet apex*.—Apiculate to acute.

*Lateral and terminal leaflet base*.—Short attenuate to rounded.

*Lateral and terminal leaflet margin*.—Biserrate.

*Lateral and terminal leaflet texture and luster, upper and lower surfaces*.—Moderately pubescent, slightly rugose; slightly glossy.

*Lateral and terminal leaflet venation pattern*.—Pinnate.

*Lateral and terminal leaflet color*.—Developing leaflets, upper surface: Close to 137A. Developing leaflets, upper surface: Close to 13813. Fully expanded leaflets, upper surface: Darker than between NN137A and 147A; venation, close to 144A. Fully expanded leaflets, lower surface: Between 147A and 147B; venation, close to 152D.

*Leaf petiole length*.—About 27 cm.

*Leaf petiole diameter*.—About 2.5 mm.

*Leaf petiole strength*.—Strong.

*Leaf petiole texture and luster, upper and lower surfaces*.—Smooth, glabrous; glossy.

*Leaf petiole color, upper surface*.—Close to 176B; distally, close to N199B.

*Leaf petiole color, lower surface*.—Close to 200D.

Flower description:

*Flower type and flowering habit*.—Numerous single rotate flowers arranged on terminal branched panicles; flowers face upright, outward or downward depending on position on the panicle; freely and uniformly flowering habit with about 1,600 flowers developing per inflorescence.

*Fragrance*.—Moderately fragrant; sweet and pleasant.

*Natural flowering season*.—Plants begin flowering about 13 weeks after planting and flower remontantly from late spring to late summer in The Netherlands.

*Postproduction longevity*.—Flowers last about ten days on the plant; flowers not persistent.

*Inflorescence height*.—About 29.5 cm.

*Inflorescence diameter*.—About 11.9 cm.

*Flower buds*.—Height: About 3 mm. Diameter: About 1.5 mm. Shape: Elliptic. Texture and luster: Smooth, glabrous; matte. Color: Close to 59A; distally, close to 71A.

*Flower diameter*.—About 1 cm.

*Flower depth*.—About 7 mm.

*Petals*.—Quantity per flower: Typically five in a single whorl. Length: About 5.5 mm. Lobe width: About 1 mm. Shape: Oblanceolate. Apex: Acute. Base: Narrowly cuneate. Margin: Entire. Texture and luster, upper and lower surfaces: Smooth, glabrous; matte. Color: Developing petals, upper and lower surfaces: Close to 71A to 71B. Fully expanded petals, upper and lower surfaces: Close to 72B; color becoming closer to N77B with development.

*Sepals*.—Quantity per flower: Typically five in a single whorl, lower 60% fused; campanulate-shaped calyx. Length: About 2.5 mm. Width: About 1.5 mm. Shape: Ovate. Apex: Acute. Margin: Entire. Texture and luster, upper and lower surfaces: Smooth, glabrous; matte. Color: Developing sepals, upper surface: Close to 59B. Developing sepals, lower surface: Close to 59A. Fully developed sepals, upper and lower surfaces: Close to 73D; fading towards the apex and margins to close to 61A and at the margins and apex, close to 59A.

*Peduncles*.—Length: About 38.1 cm. Diameter: About 2.5 mm. Angle: Erect. Strength: Strong. Texture and luster: Moderately pubescent; slightly glossy. Color: Between 187A and 200B.

*Pedicels*.—Length: About 1 mm. Diameter: About 0.5 mm. Angle: About 40° from peduncle axis. Strength: Moderately strong. Texture and luster: Moderately pubescent; matte. Color: Close to 61A.

*Reproductive organs*.—Stamens: Quantity per flower: About ten. Filament length: About 3.5 mm. Filament color: Close to 71B. Anther shape: Broadly ovate; basifixed. Anther size: About 0.3 mm by 0.2 mm. Anther color: Close to 68C to 68D. Pollen amount: Scarce. Pollen color: Close to 156D. Pistils: Quantity per flower: Two. Pistil length: About 1.5 mm. Style length: About 1 mm. Style color: Close to 71A. Stigma diameter: About 0.1 mm. Stigma shape: Club-shaped. Stigma color: Close to 71A. Ovary color: Close to 60B.

*Seeds and fruits*.—To date, seed and fruit development have not been observed on plants of the new *Astilbe*.

Pathogen & pest resistance: Plants of the new *Astilbe* have not been noted to be resistant to pathogens and pests common to *Astilbe* plants.

Garden performance: Plants of the new *Astilbe* have been observed to have good garden performance and tolerate rain, wind, low temperatures about −25° C. and high temperatures about 35° C. and to be suitable for USDA Hardiness Zones 5 to 10.

It is claimed:

1. A new and distinct *Astilbe* plant named 'Vision Vulcano' as illustrated and described.

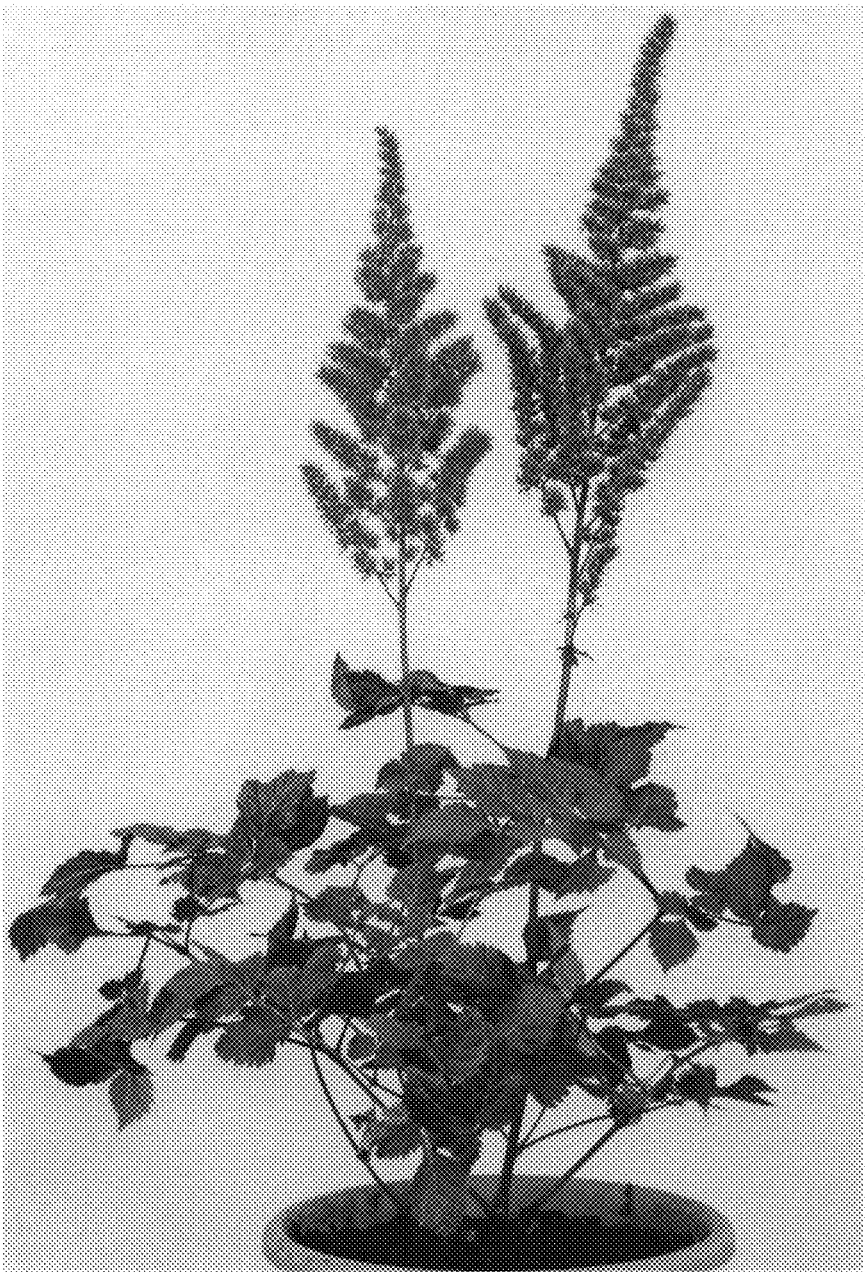

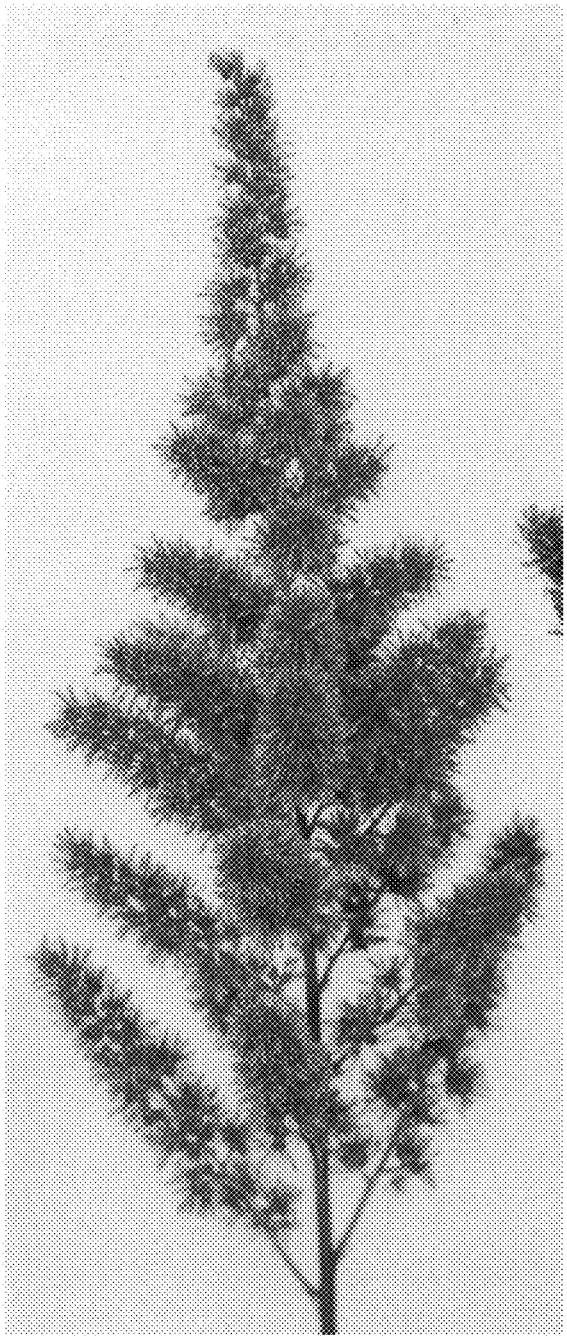

* * * * *